United States Patent [19]

Mulholland

[11] Patent Number: 5,741,239
[45] Date of Patent: *Apr. 21, 1998

[54] INTRA-RECTAL DRAIN AND RECEPTACLE FOR FECAL INCONTINENCE

[76] Inventor: Kevin J. Mulholland, R.R. 1, Box 2522, Huntington, Vt. 05462

[*] Notice: The term of this patent shall not extend beyond the expiration date of Pat. No. 5,520,669.

[21] Appl. No.: 653,621

[22] Filed: May 24, 1996

Related U.S. Application Data

[63] Continuation-in-part of Ser. No. 276,354, Jul. 19, 1994, Pat. No. 5,520,669.
[51] Int. Cl.⁶ ............................................. A61F 5/44
[52] U.S. Cl. ........................... 604/328; 604/348; 604/355
[58] Field of Search .................................. 604/348, 355, 604/327–331, 337; 600/29–31; 601/197

[56] References Cited

U.S. PATENT DOCUMENTS

| | | | |
|---|---|---|---|
| 3,548,828 | 12/1970 | Vasile | 604/328 |
| 3,918,452 | 11/1975 | Cornfield | 604/286 |
| 3,938,521 | 2/1976 | Ritota et al. | 604/328 |
| 3,964,111 | 6/1976 | Packer | 604/355 |
| 4,030,500 | 6/1977 | Ronnquist | 604/328 |
| 4,067,335 | 1/1978 | Silvanov | 604/328 |
| 4,117,847 | 10/1978 | Clayton | 604/328 |
| 4,182,332 | 1/1980 | Delaney | 604/328 |
| 5,261,898 | 11/1993 | Polin et al. | 604/328 |
| 5,520,669 | 5/1996 | Mulholland | 604/328 |

*Primary Examiner*—Mark O. Polutte
*Attorney, Agent, or Firm*—Donald W. Meeker

[57] ABSTRACT

A rubberized sealing ring has a flat smooth broad bottom sealing surface for sealing with and spreading the pressure over an area of the rectal mucosal tissue. A peaked top surface has a wide inwardly sloping face for funneling the fecal matter into a tapering funnel-shaped neck. The sealing ring compresses together in a linear shape for anal insertion and expands resiliently into a sealing ring inside the patient past the interior anal sphincter. An external receptacle connects to the neck for collecting excretions. The receptacle may be formed integrally with the neck and sealing ring or may be detachable. A gas release valve is built into the top of the receptacle. An enema tube may be inserted in the neck. A spring may be built into the center of the sealing ring. A coil spring, flat spring, or combination spring may be used. Reinforcement on two sides of the sealing ring facilitates collapse of the sealing ring on the non-reinforced sides into a linear configuration by pulling on the neck for easy removal of the device from the patient. A slotted tube with a plunger and handle may be used to insert the compressed sealing ring into the anal opening of a patient. The sealing ring, neck, and receptacle are formed of a non-alergenic polymer, such as LATEX®.

15 Claims, 3 Drawing Sheets

INTRA-RECTAL DRAIN AND RECEPTACLE FOR FECAL INCONTINENCE

REFERENCE TO RELATED PATENT APPLICATION

This is a continuation-in-part of patent application Ser. No. 08/276,354 filed Jul. 19, 1994 now U.S. Pat. No. 5,520,669.

BACKGROUND OF THE INVENTION

1. Technical Field

The present invention relates to a medical device related to fecal incontinence and in particular to a fecal collection receptacle connected by a flexible tube to an insertable broad low pressure intra-rectal sealing ring.

2. Description of the Prior Art

Fecal incontinence is a medical problem which causes much discomfort, embarrassment, and loss of self-esteem for patients and causes irritation and considerable work for health care staff. Elderly patients are especially prone to this problem, with sometimes over half of geriatric patients in care facilities having occasional fecal incontinence problems and often over ten percent having persistent fecal incontinence problems.

Causes for fecal incontinence vary from treatable situations of fecal incontinence caused by fecal stasis and some physical diseases such as carcinoma of the rectum and colon and ischemic colitis or diverticular disease, to untreatable fecal incontinence caused by neurologic disorders such as dementia, and physical diseases such as megacolon, Crohn's disease, and rectal prolapse. Drugs such as analgesics and hematinics and excessive use of purgatives can also cause fecal incontinence.

In untreatable cases, trying to contain the fecal matter as it is excreted seems to be the primary goal to save embarrassment and considerable mess. Diapers are not the best solution since there is still a considerable mess and cleanup care associated with the contained mess in the diapers, as well as occasional leakage problems out of the diapers. All the external fecal collection means have a similar problem of still having a contained localized mess and periodic leakage.

Other fecal incontinence devices which are inserted in the rectum tend to be harsh on tissues and cause irritation and potential infection problems. Prolonged use of such devices is generally not possible due to the damage caused by the devices themselves. U.S. Pat. No. 3,938,521 describes a fecal collecting bag with an insertable collar which is inflated to form a donut-shaped collar. Such a donut-shaped inflated collar would not lie flat against the rectal mucosal tissue and, therefore, would not provide a good seal and would likely permit leakage around the outside of the collar. The relatively small area of the collar contacting the rectal mucosal tissue would be likely to cause irritation and infection of the tissue.

U.S. Pat. No. 4,182,332 shows an insertable rectal catheter with a series of flanges contacting the rectal mucosal tissue, which would be likely to cause leakage, irritation, and infection of the tissue.

U.S. Pat. No. 4,067,335 provides a fecal matter collecting unit with an insertable funnel with a series of ribs contacting the rectal mucosal tissue allowing leakage and putting too much pressure on the tissue adjacent to each rib which would cause irritation and infection.

DISCLOSURE OF THE INVENTION

The present invention provides, on a fecal collection receptacle and tapered neck, a broad-lipped sealing ring with a bottom broad smooth flat sealing rim surface for contacting the rectal mucosal tissue. The smooth flat sealing rim surface distributes the pressure over the rectal mucosal tissue area contacted by the sealing rim surface so that it creates only a low pressure thereon, which is less than the mean arterial pressure of approximately 100 mm Hg. This low pressure would not cut off the blood supply and would avoid ulcerated tissue, a major drawback of previous devices. The smooth flat sealing rim lies flat against the tissue creating a tight seal to prevent leakage while exerting low pressure. A long sloping inner top of the broad-lipped sealing ring would funnel material into the chute and fecal collection bag.

By fabricating the broad-lipped sealing ring of a flexible rubberized material, the sealing ring is easily compressed flat with the sealing ring forming a slightly arched linear configuration for insertion of the sealing ring into the anus of the patient. Once inserted past the anal sphincter, the sealing ring would then unfurl purposefully to open the sealing ring to its normal annular shape and cause the sealing ring to lie open with the smooth flat sealing rim surface pressing flat against the rectal mucosal tissue to form a water-tight seal on the interior of the pelvic diaphragm surrounding the opening above the internal anal sphincter. This occludes the external anal sphincter and allows feces to flow from the rectum through the annular sealing ring, passing through the cone-shaped tapered neck into an external receptacle. External fecal soiling would be circumvented and the waste matter would be confined within the system, never contacting the skin of the patient or any external clothing or bed covers. A coiled or flat spring within the broad lipped sealing ring would further enhance the flexibility of the ring for compression and automatic unfurling.

Reinforcing two opposite sides of the sealing ring and leaving the other two opposing sides without reinforcement creates a sealing ring that would automatically be pulled into a linear shape by tugging on the neck of the invention enabling the device to be removed easily from the patient by simply tugging on the neck of the invention causing the sealing ring to collapse into a linear shape and slip easily out of the rectum of the patient.

A piston moved by a handle through a slotted cylinder could facilitate insertion of the sealing ring in its compressed flat linear shape requiring less contacting of the skin of the patient and could provide improved user friendliness.

The flexibly tapered neck extending downwardly from the sealing ring into the external flexible receptacle enables the receptacle to be positioned as desired to enable a patient to walk around by strapping the receptacle to the leg of the patient. The receptacle may be fabricated of a variety of materials in a variety of shapes to suit the needs of the patient. Along the top of the receptacle, a gas release valve prevents the receptacle from filling with gas and thereby avoids stretching or breaking the receptacle.

Inserting a tube into the tapered neck of the invention presents a closed system for giving enemas with a built-in receptacle and closed system to contain all of the liquid and fecal matter with no possibility of creating a mess.

Constructing the invention of LATEX® or other non-allergenic pliable material creates a relatively inexpensive, but very effective fecal collection device which may be removed and disposed of, requiring no contact with the fecal matter. The ease of insertion of the device makes replacement with an empty clean fecal collector no problem.

BRIEF DESCRIPTION OF THE DRAWINGS

These and other details of my invention will be described in connection with the accompanying drawings, which are furnished only by way of illustration and not in limitation of the invention, and in which drawings.

BEST MODE FOR CARRYING OUT THE INVENTION

Figure 1:
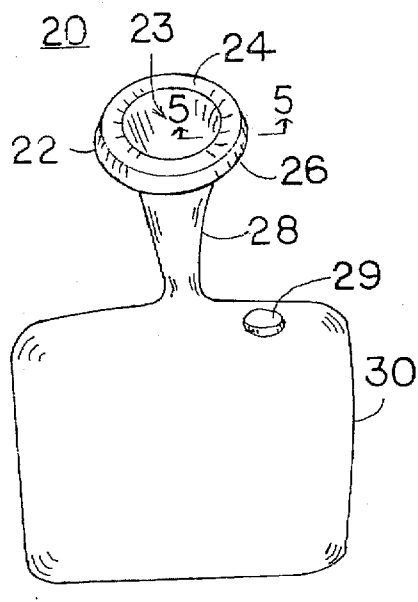
FIG. 1 is a perspective view of the preferred embodiment of the invention with the sealing ring open.

In FIGS. 1, 2, 3, 5, 12, and 13 an intra-rectal drain and receptacle for fecal incontinence 20 comprises a rubberlike springy annular sealing ring 22 having a broad flat bottom surface constituting a broad flat smooth sealing surface 40 (in FIG. 5) and an inwardly sloping upper surface 24 forming a funnel. The sealing ring 22 may be squeezed closed as in FIG. 2 for insertion into the anus of the patient and allowed to spring open inside the patient as in FIG. 3. Extending downwardly from the sealing ring, a resilient water-tight collapsible neck 28 tapers downwardly in a funnel shape from the sealing ring. Flexibly connected with a water-tight connection to the neck, a resilient water-tight receptacle 30 receives and stores the waste matter for disposal. A gas release valve 29 is built into the receptacle 30 adjacent to the top of the receptacle. The gas release valve could be a double rubber flap arrangement or any type of valve allowing a one-way outward release of gas and not liquid. The broad flat bottom of the sealing ring forming the broad flat smooth sealing surface 40 presses gently with less than arterial pressure against the tissue above the internal anal sphincter to create a positive seal against leakage. The inwardly sloping top surface 24 of the sealing ring directs waste into the opening 23 and down the funnel-like resilient neck 28 into the receptacle 30.

Figure 5:
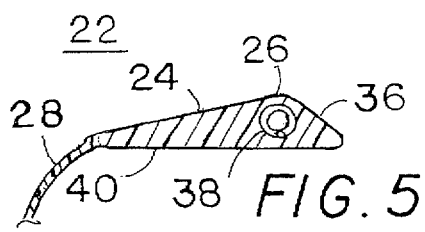
FIG. 5 is an exploded cross-sectional view of the sealing ring of the invention taken through 5—5 of FIG. 1 showing the spring imbedded in the sealing ring.
Figure 10:
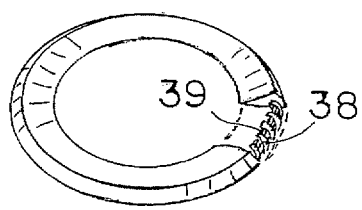
FIG. 10 is a perspective view in partial section showing an alternate embodiment of the invention with a combined flat spring and coiled spring.
Figure 12:
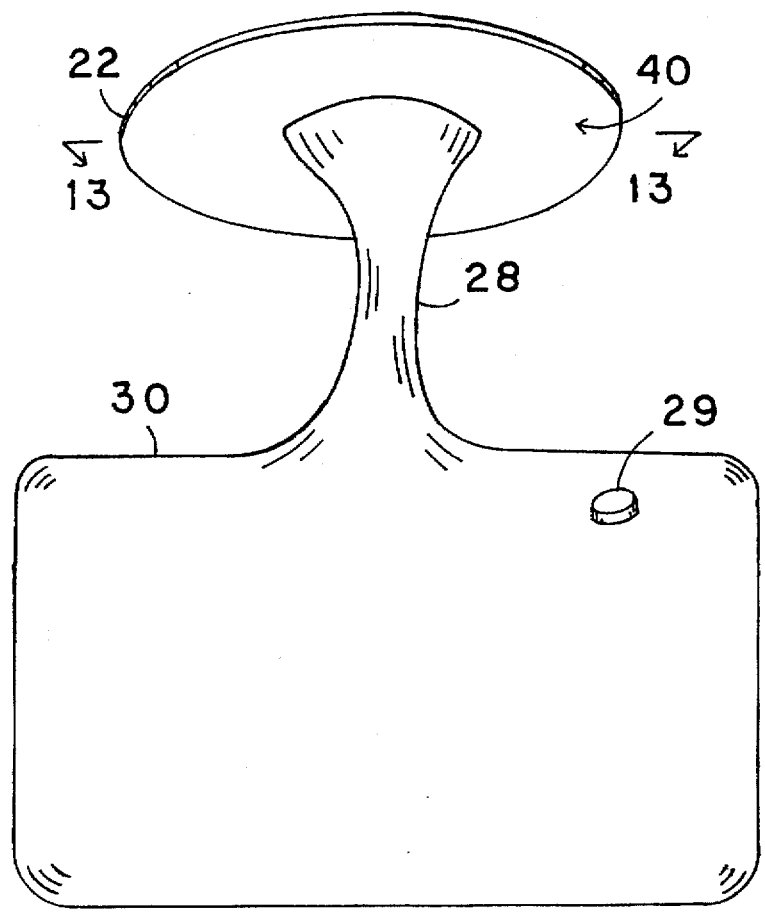
FIG. 12 is an enlarged perspective view of the preferred embodiment of the invention showing the broad flat smooth bottom sealing surface of the sealing ring.
Figure 13:
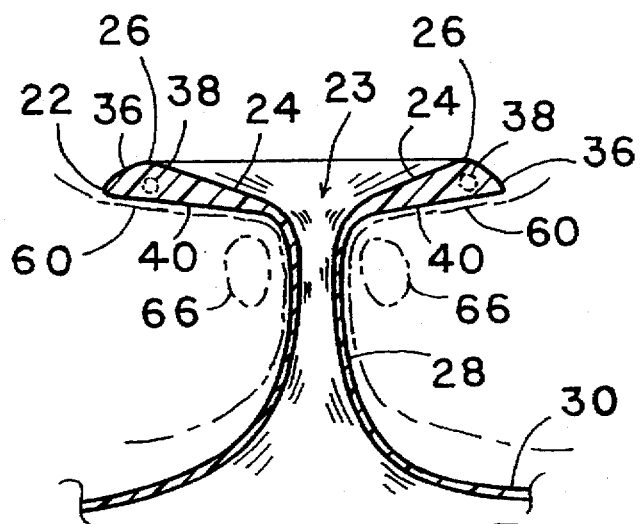
FIG. 13 is a partial cross-sectional view taken through 13—13 of FIG. 12 showing the invention in place in the body of the patient.

In FIGS. 5, 12, and 13 the sealing ring 22 is substantially triangular in cross-section with the widest side on the bottom forming the broad flat smooth sealing surface 40 and two unequal sides 24 and 36 on the top forming a peak 26 with the wider top side 24 on the interior of the annular sealing ring sloping inwardly toward the center of the annular sealing ring. Inside the sealing ring under the peak 26, a spring 38 may be imbedded in the sealing ring 22. The spring may be a coil spring 38 as in FIGS. 5 and 7, a flat spring 39 as in FIG. 8, or a flat spring 39 and a coiled spring 38 combined together as in FIG. 10.

In FIG. 13, the broad flat smooth bottom sealing surface 40 is shown contacting the rectal mucosal tissue 60 (shown dashed) over a broad area of the rectal mucosal tissue 60 adjacent to the anal sphincter muscles 66 spreading the pressure over the broad area while creating a water-tight seal between the broad flat smooth bottom sealing surface 40 of the sealing ring 22 and the rectal mucosal tissue 60.

Figure 4:
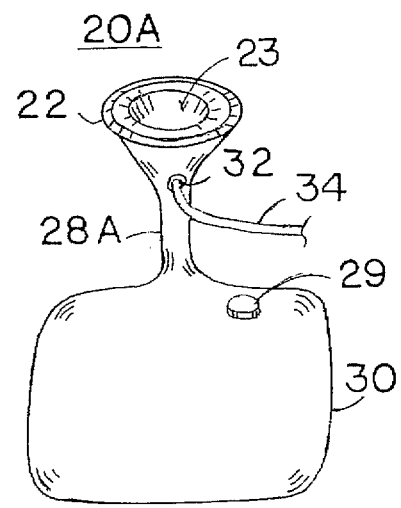
FIG. 4 is a perspective view of an alternate embodiment of the invention having an enema tube inserted into the neck of the invention.

In FIG. 4 an enema tube 34 may be inserted in the tapering neck in a water-tight connection 32, and enema solution may be pumped through the tube 34 into the neck 28 and on into the colon of the patient. With this enclosed system there is no mess created in the process of giving the enema.

Figure 2:
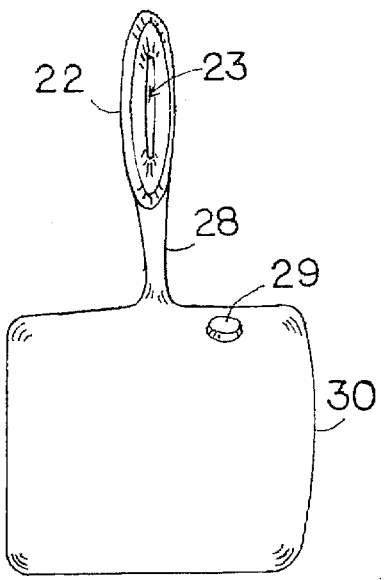
FIG. 2 is a perspective view of the invention with the sealing ring closed for insertion in a patient.
Figure 3:
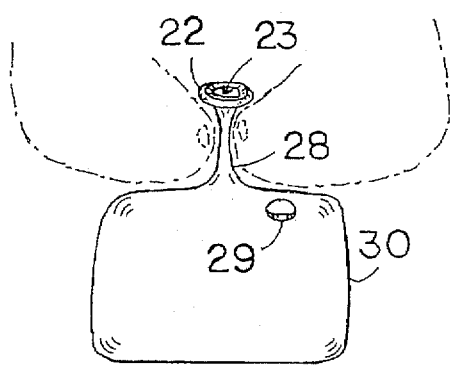
FIG. 3 is a perspective view showing the invention installed in the body of a patient.
Figure 11:
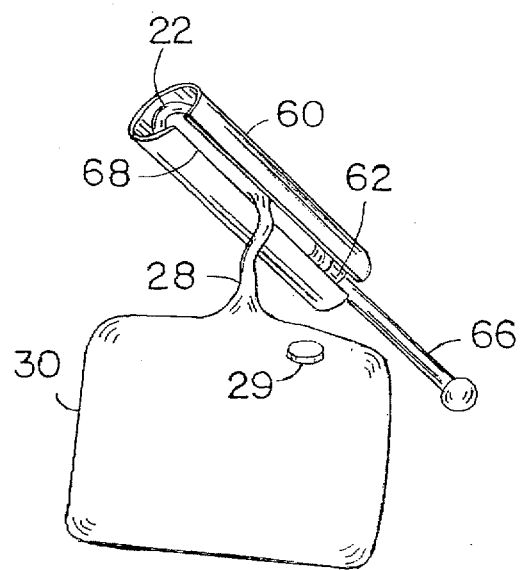
FIG. 11 is a perspective view showing an insertion tube used to install the invention in a patient.

The sealing ring 22 may be squeezed together as in FIG. 2 and inserted by hand or, as in FIG. 11, insertion may be accomplished by using a tube 60 having a longitudinal slot and a plunger 62 with a handle 66 at one end of the tube. The sealing ring 22 is squeezed together into a linear shape, inserted in the tube 60 with the neck 28 protruding out through the slot, and the handle 66 pushed causing the plunger to insert the sealing ring 22 into the rectal opening of a patient.

Figure 6:
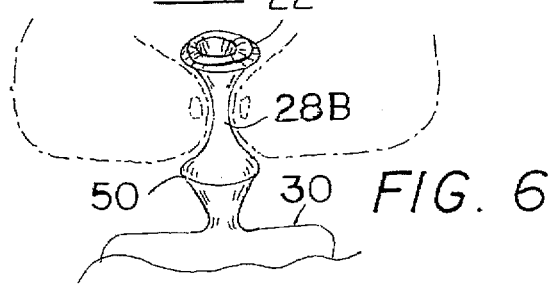
FIG. 6 is a perspective view of an alternate embodiment of the invention with a second ring outside the patient.

In FIG. 6 an alternate embodiment of the invention 20B shows a second ring 50 around the neck 28 spaced apart from the first sealing ring 22 so that when the first sealing ring 22 is inserted into an anus (shown dashed) of a patient with the first sealing ring 22 opening past an interior anal sphincter of the patient, the second ring 50 will remain just outside the anus so that the two rings hold the invention in place to prevent slippage of the invention in or out.

Figure 9:
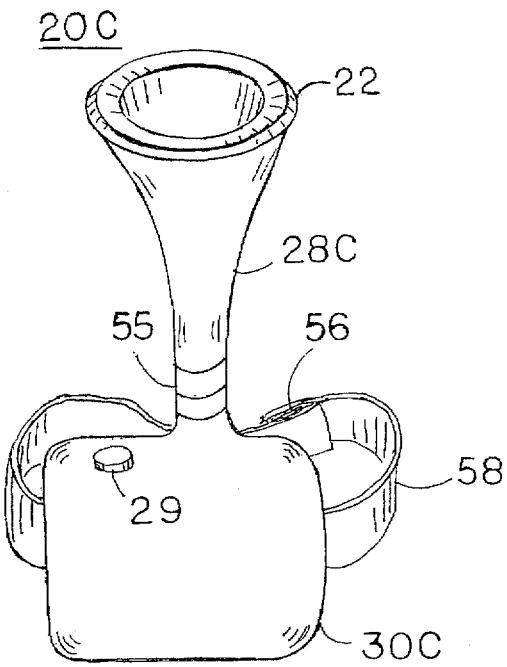
FIG. 9 is a perspective view of an alternate embodiment of the invention having a removable receptacle attached to the neck of the invention.

The sealing ring 22 and neck 28 and receptacle 30 may be fabricated in one piece by molding a flexible non-allergenic polymer, such as LATEX®. This is primarily intended as a disposable item. Alternately, as in FIG. 9, the receptacle 30C is removably attached by a water-tight connection 55 to the neck 28C. The receptacle is disposed of and replaced by an empty receptacle. The receptacle may be fitted with a leg strap 58 adjustably attached by VELCRO® fasteners 56 or other means to a leg of a patient for greater mobility. The receptacle may be shaped to suit any desired usage by a patient.

Figure 7:
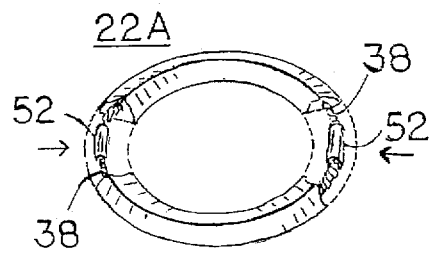
FIG. 7 is a perspective view in partial section showing an alternate embodiment of the sealing ring with two opposing sides of the sealing ring reinforced.
Figure 8:
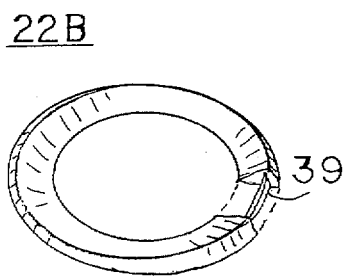
FIG. 8 is a perspective view in partial section showing an alternate embodiment of the invention with a flat spring.

In FIG. 7, the sealing ring 22A is reinforced on two opposing sides of the sealing ring with a restricting band 52 around a portion of the spring 38, so that pulling on the neck of the sealing ring, when the sealing ring is in place inside a patient will cause two non-reinforced sides of the sealing ring to collapse inwardly pulling the sealing ring into a linear shape allowing the sealing ring to slip easily out of the patient.

It is understood that the preceding description is given merely by way of illustration and not in limitation of the invention and that various modifications may be made thereto without departing from the spirit of the invention as claimed.

What is claimed is:

1. An intra-rectal drain and receptacle device for fecal incontinence having an insertable sealing ring with a wide flat smooth bottom annular sealing surface which rests on and distributes pressure over a substantial area of a patient's rectal mucosal tissue creating a seal therebetween, the device comprising:

a rubberlike springy annular sealing ring having a broad smooth flat annular bottom sealing surface with a large surface area which is adapted to rest on and distribute pressure over the substantial area of the patient's rectal mucosal tissue for laying flat against the tissue on the interior of the pelvic diaphragm for surrounding the opening above the internal anal sphincter for occluding the external anal sphincter and for allowing fecal matter to flow from the rectum through the annular sealing ring for creating a water-tight seal between the device and the mucosal tissue to prevent leakage while being capable of exerting low pressure on the mucosal tissue so that the device does not cut off the blood supply and avoids irritated and ulcerated tissue, and a wide inwardly sloping upper surface for directing the fecal matter through the sealing ring, which annular sealing ring is collapsible to a linear configuration and automatically expansible to an annular configuration;

a resilient water-tight collapsible neck extending downwardly from the sealing ring and attached thereto by a water-tight connecting means, the neck tapering downwardly in a funnel shape from the sealing ring;

a resilient water-tight receptacle flexibly connected to the neck with a water-tight seal so that the fecal matter would be confined within the system, never contacting the skin of the patient or any external clothing or bed covers.

2. The device of claim 1 wherein the broad smooth flat annular bottom sealing surface has a sufficiently broad surface area of contact so that it is capable of exerting a pressure on the substantial area of the patient's rectal mucosal tissue which is less than mean arterial pressure.

3. The device of claim 2 wherein the sealing ring is substantially triangular in cross-section with a broad bottom forming the broad smooth flat annular bottom sealing surface and two unequal sides on the top forming a peak with a wide top side on the interior of the annular sealing ring sloping downwardly toward the center of the annular sealing ring to facilitate the unimpeded flow of fecal matter.

4. The device of claim 3 further comprising an annular spring imbedded inside the sealing ring under the peak.

5. The device of claim 4 wherein the spring is a coil spring.

6. The device of claim 4 wherein the spring is a flat spring.

7. The device of claim 4 wherein the spring is a flat spring and a coil spring combined together.

8. The device of claim 3 wherein the receptacle is further provided with a gas release valve.

9. The device of claim 3 further comprising a tube inserted in the tapering neck in a water-tight connection, so that an enema solution may be pumped through the tube into the neck.

10. The device of claim 3 further comprising a second ring around the neck spaced apart from the first sealing ring so that when the first sealing ring is inserted in the anus of the patient with the first sealing ring opening past an interior anal sphincter of the patient, the second ring will remain just outside the anus so that the two rings hold the device in place.

11. The device of claim 3 wherein the sealing ring and neck and receptacle are fabricated in one piece by molding a flexible non-alergenic polymer.

12. The device of claim 3 wherein the sealing ring is reinforced on two opposing sides of the sealing ring, so that pulling on the neck of the sealing ring, when the sealing ring is in place inside a patient, will cause two intermediate non-reinforced sides of the sealing ring to collapse inwardly pulling the sealing ring into a linear shape allowing the sealing ring to slip out of the patient.

13. The device of claim 3 wherein the receptacle is removably attached by a water-tight connection to the neck.

14. The device of claim 13, wherein the receptacle is adapted to be strapped to the leg of a patient.

15. An intra-rectal drain and receptacle and insertion tube for fecal incontinence having an insertable sealing ring with a wide flat smooth bottom annular sealing surface which rests on and distributes pressure over a substantial area of a patient's rectal mucosal tissue creating a seal therebetween, the device comprising:

a rubberlike springy annular sealing ring having a broad smooth flat annular bottom sealing surface with a large surface area which is adapted to rest on and distribute pressure over the substantial area of the patient's rectal mucosal tissue for laying flat against the tissue on the interior of the pelvic diaphragm for surrounding the opening above the internal anal sphincter for occluding the external anal sphincter and for allowing fecal matter to flow from the rectum through the annular sealing ring for creating a water-tight seal between the device and the mucosal tissue to prevent leakage while being capable of exerting low pressure on the mucosal tissue so that the device does not cut off the blood supply and avoids irritated and ulcerated tissue, and a wide inwardly sloping upper surface for directing the fecal matter through the sealing ring, which annular sealing ring is collapsible to a linear configuration and automatically expansible to an annular configuration;

a resilient water-tight collapsible neck extending downwardly from the sealing ring and attached thereto by a water-tight connecting means, the neck tapering downwardly in a funnel shape from the sealing ring;

a resilient water-tight receptacle flexibly connected to the neck with a water-tight seal so that the fecal matter would be confined within the system, never contacting the skin of the patient or any external clothing or bed covers;

wherein the broad smooth flat annular bottom sealing surface has a sufficiently broad surface area of contact so that it is capable of exerting a pressure on the substantial area of the patient's rectal mucosal tissue which is less than mean arterial pressure;

wherein the sealing ring is substantially triangular in cross-section with a broad bottom forming the broad smooth flat annular bottom sealing surface and two unequal sides on the top forming a peak with a wide top side on the interior of the annular sealing ring sloping downwardly toward the center of the annular sealing ring to facilitate the unimpeded flow of fecal matter; and an insertion tube having a longitudinal slot and a plunger with a handle at one end of the tube, so that the sealing ring may be squeezed together into a linear shape, inserted in the tube with the neck of the sealing ring protruding out through the slot, so that pushing the plunger inserts the sealing ring into the rectal opening of the patient.

* * * * *